United States Patent [19]

Gelotte et al.

[11] 4,264,609

[45] Apr. 28, 1981

[54] N-[3-DIMETHYLAMINO-2-(4-PYRIDINYL)-2-PROPENYLIDENE]-N-METHYLMETHANIMINIUM CHLORIDE HYDROCHLORIDE, ITS USE IN PREPARING 5-(CYANO OR CARBAMYL)-[3,4'-BIPYRIDIN]-6(1H)-ONE AND ITS USE AS A CARDIOTONIC

[75] Inventors: Karl O. Gelotte, Nassau; Chester J. Opalka, Jr., Schodack, both of N.Y.

[73] Assignee: Sterling Drug Inc., New York, N.Y.

[21] Appl. No.: 124,808

[22] Filed: Feb. 26, 1980

[51] Int. Cl.³ .................... C07D 213/53; A61K 31/44
[52] U.S. Cl. .................................... 546/249;
546/329; 546/257; 546/258
[58] Field of Search ................. 546/329, 249; 424/263

[56] References Cited

U.S. PATENT DOCUMENTS

| | | | |
|---|---|---|---|
| 4,004,012 | 1/1977 | Lesher et al. | 424/263 |
| 4,072,746 | 2/1978 | Lesher et al. | 546/257 X |
| 4,107,315 | 8/1978 | Lesher et al. | 546/257 X |

OTHER PUBLICATIONS

Nantkanomirski et al., "Current Abstracts of Chemistry", vol. 74, Issue 814, (1979), item 285573.
Arnold; Coll. Czech. Chem. Comm. 28, (1963), pp. 863–868.

*Primary Examiner*—Joseph Paul Brust
*Attorney, Agent, or Firm*—Robert K. Bair; B. Woodrow Wyatt

[57] ABSTRACT

Amrinone intermediates are prepared by reacting 4-picoline with at least three mole equivalents of phosgene per mole of 4-picoline and excess dimethylformamide to produce N-[3-dimethylamino-2-(4-pyridinyl)-2-propenylidene]-N-methylmethaniminium chloride hydrochloride, then reacting the latter with Q-$CH_2CONH_2$ and at least three mole equivalents of base in anhydrous medium and then neutralizing the reaction mixture to produce 5-Q-[3,4'-bipyridin]-6(1H)-one, where Q is cyano or carbamyl. Other aspects of the invention are the separate steps of preparing said iminium salt and then converting it to said 5-Q-[3,4'-bipyridin]-6(1H)-one, and also cardiotonic composition and method for increasing cardiac contractility using said iminium salt or pharmaceutically-acceptable acid-addition salt thereof as the active cardiotonic.

14 Claims, No Drawings

N-[3-DIMETHYLAMINO-2-(4-PYRIDINYL)-2-PROPENYLIDENE]-N-METHYLMETHANIMINIUM CHLORIDE HYDROCHLORIDE, ITS USE IN PREPARING 5-(CYANO OR CARBAMYL)-[3,4'-BIPYRIDIN]-6(1H)-ONE AND ITS USE AS A CARDIOTONIC

CROSS-REFERENCE TO RELATED APPLICATIONS

Copending K. O. Gelotte and E. D. Parady U.S. Patent Application Ser. No. 124,807, filed Feb. 26, 1980, discloses and claims the process which comprises reacting 4-picoline below about 30° C. with at least three mole equivalents of an inorganic acid halide, preferably phosphorus oxychloride, per mole of 4-picoline and excess dimethylformamide, reacting in solution the unisolated resulting N-[3-dimethylamino-2-(4-pyridinyl)-2-propenylidene]-N-methylmethaniminium salt (after adjusting the pH to about 8.0 and filtering off the precipitated inorganic cationic salts) with excess α-cyanoacetamide followed by at least three mole equivalents of base and then isolating 5-cyano-[3,4'-bipyridin]-6(1H)-pyridinone in free base form (after neutralization) or in the form of its inorganic cationic salt.

Copending C. J. Opalka, Jr. and G. Y. Lesher U.S. Patent Application Ser. No. 60,758, filed July 26, 1979, now U.S. Pat. No. 4,223,149, issued Sept. 16, 1980, discloses and claims, inter alia, the process which comprises reacting β-(dimethylamino)-α-(4-pyridinyl)acrolein [alternatively named 3-dimethylamino-2-(4-pyridinyl)-2-propen-1-one] in a lower alkanol to produce 1,2-dihydro-2-oxo-5-(4-pyridinyl)nicotinonitrile, that is, the same as 3-cyano-5-(4-pyridinyl)-2(1H)-pyridinone or alternatively named 5-cyano-[3,4'-bipyridin]-6(1H)-one.

BACKGROUND OF THE INVENTION (a) Field of the Invention

This invention relates to a novel method for preparing 5-Q-[3,4'-bipyridin]-6(1H)-one where Q is cyano or carbamyl, a novel intermediate used therein and its preparation, and to the use of said novel intermediate or salt in a cardiotonic composition or method for increasing cardiac contractility.

(b) Description of the Prior Art

Lesher and Opalka U.S. Pat. No. 4,004,012, issued Jan. 18, 1977, shows two methods of preparing 1,2-dihydro-2-oxo-5-(pyridinyl)nicotinonitriles and conversion by hydrolysis to the corresponding nicotinamides, one method of preparing 1,2-dihydro-2-oxo-5-(pyridinyl)-nicotinamides, and, in turn, the conversion of the nicotinamides to the corresponding 3-amino compounds. These methods are presented structurally in columns 3 and 4 of U.S. Pat. No. 4,004,012. Two methods are disclosed for preparing 1,2-dihydro-2-oxo-5-(pyridinyl)-nicotinonitriles (III in patent), i.e., (1) by reacting α-(pyridinyl)-β-(R₁R₂N)acrolein (II in patent) with α-cyanoacetamide in the presence of a basic condensing agent, preferably an alkali lower-alkoxide, e.g., sodium methoxide or sodium ethoxide, in a lower-alkanol, e.g., methanol or ethanol; and, (2) by heating α-(pyridinyl)-malonaldehyde with α-cyanoacetamide in the presence of a catalytic condensing agent, preferably morpholine or piperidine and/or its acetate. As shown in Example A-1 in the paragraph common to columns 9 and 10 of U.S. Pat. No. 4,004,012, the product in method (1) is collected as its sodium salt, recrystallized and then converted by treatment with hydrochloric acid to 1,2-dihydro-2-oxo-5-(pyridinyl)nicotinonitrile. Also disclosed is a method of preparing 1,2-dihydro-2-oxo-5-(pyridinyl)nicotinamides by reacting α-(pyridinyl)-β-(R₁R₂N)acrolein with malonamide.

A recently published abstract ["Current Abstracts of Chemistry", Vol. 74, Issue 814, Item 285573, 1979] of a Polish publication [Nantkanomirski and Kaczmarek, Polish J. Pharmacol. Pharmacy 30(5), 707–12 (1978)] shows, inter alia, the reaction of 3-dimethylamino-2-(4-pyridinyl)acrolein [same as β-(dimethylamino)-α-(4-pyridinyl)acrolein] with malononitrile in the presence of sodium methoxide in methanol to produce 2-methoxy-5-(4-pyridinyl)nicotinonitrile.

Arnold [Coll. Czech. Chem. Comm. 28, 863–868 (1963)] shows the preparation of β-dimethylamino-α-(4-pyridinyl)acrolein by three different methods: (a) formylation of 4-picoline with dimethylformamide and phosphorus oxychloride; (b) formylation of 4-picoline with dimethylformamide and phosgene in chloroform; and, (c) formylation of 4-(2-dimethylaminovinyl)pyridine with dimethylformamide and phosgene in chloroform.

SUMMARY OF THE INVENTION

The invention relates in one aspect to the process which comprises the steps of first reacting 4-picoline with at least three mole equivalents of phosgene per mole of 4-picoline and excess dimethylformamide to produce N-[3-dimethylamino-2-(4-pyridinyl)-2-propenylidene]-N-methylmethaniminium chloride hydrochloride and then reacting the latter intermediate salt with Q—CH₂CONH₂ and base in anhydrous medium to produce 5-Q-[3,4'-bipyridin]-6(1H)-one, where Q is cyano or carbamyl, both of which are known intermediates for preparing the cardiotonic, amrinone. In other aspects, the invention relates to said intermediate N-[3-dimethylamino-2-(4-pyridinyl)-2-propenylidene]-N-methylmethaniminium chloride hydrochloride or other salt, also useful as a cardiotonic agent, to the above process for its preparation, and, to the above process for its conversion to 5-Q-[3,4'-bipyridin]-6(1H)-one.

DETAILED DESCRIPTION INCLUSIVE OF PREFERRED EMBODIMENTS

In a composition aspect the invention resides in N-[3-dimethylamino-2-(4-pyridinyl)-2-propenylidene]-N-methylmethaniminium salt having formula I

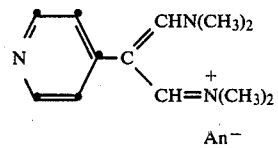

where An⁻ is an anion of a pharmaceutically-acceptable acid, or a pharmaceutically-acceptable acid addition salt thereof. This compound not only is useful as an intermediate, as seen hereinbelow, but also surprisingly was found to have cardiotonic activity when tested by a standard cardiotonic test procedure. The preferred free base form has formula I where An⁻ is Cl⁻, viz., N-[3-dimethylamino-2-(4-pyridinyl)-2-propenylidene]-N-methylmethaniminium chloride, and its preferred acid-addition salt is its hydrochloride, namely, N-[3- dimethylamino-2-(4-pyridinyl)-2-propenylidene]-N-methylmethaniminium chloride hydrochloride.

One process aspect of the invention resides in the process which comprises reacting 4-picoline with at least three mole equivalents of phosgene per mole of 4-picoline and excess dimethylformamide to produce said N-[3-dimethylamino-2-(4-pyridinyl)-2-propenylidene]-N-methylmethaniminium chloride hydrochloride (HCl salt of I where An⁻ is chloride).

In another process aspect the invention resides in the process which comprises reacting N-[3-dimethylamino-2-(4-pyridinyl)-2-propenylidene]-N-methylmethaniminium chloride hydrochloride with Q—CH$_2$CONH$_2$ and at least three mole equivalents of base in anhydrous medium and then neutralizing the reaction mixture to produce 5-Q-[3,4'-bipyridin]-6(1H)-one where Q is cyano or carbamyl respectively, both products being known intermediates for preparing the cardiotonic, amrinone, viz., 5-amino-[3,4'-bipyridin]-6(1H)-one.

In another process aspect the invention resides in the process which comprises the steps of first reacting 4-picoline with at least three mole equivalents of phosgene per mole of 4-picoline and excess dimethylformamide to produce N-[3-dimethylamino-2-(4-pyridinyl)-2-propenylidene]-N-methylmethaniminium chloride hydrochloride and then reacting it with Q—CH$_2$CONH$_2$ and at least three mole equivalents of base in an anhydrous medium and then neutralizing the reaction mixture to produce 5-Q-[3,4'-bipyridin]-6(1H)-one. An unexpected advantage of this process is that the precipitation in the first step provides almost quantitive yields of N-[3-dimethylamino-2-(4-pyridinyl)-2-propenylidene]-N-methylmethaniminium chloride hydrochloride, thereby obviating the need for an aqueous quench and neutralization as heretofore done to produce the previously used intermediate β-dimethylamino-α-(4-pyridinyl)acrolein. Also the near quantitative yield in the first step substantially contributes to the high overall yields in this two step process. After separation from the reaction mixture, either by filtration or by removing the supernatant reaction liquors, the intermediate N-[3-dimethylamino-2-(4-pyridinyl)-2-propenylidene]-N-methylmethaniminium chloride hydrochloride can be reacted directly in situ in the next step with Q—CH$_2$CONH$_2$ and base.

A composition aspect of the invention resides in a cardiotonic composition for increasing cardiac contractility, said composition comprising a pharmaceutically-acceptable inert carrier and, as the active component thereof, an effective amount of the cardiotonic N-[3-dimethylamino-2-(4-pyridinyl)-2-propenylidene]-N-methylmethaniminium salt (I) or pharmaceutically-acceptable acid-addition salt thereof. In a preferred embodiment of this aspect of the invention there is used as the cardiotonic N-[3-dimethylamino-2-(4-pyridinyl)-2-propenylidene]-N-methylmethaniminium chloride or pharmaceutically-acceptable acid addition salt thereof, preferably the hydrochloride.

Another aspect of the invention resides in the method for increasing cardiac contractility in a patient requiring such treatment which comprises administering orally or parenterally in a solid or liquid dosage form to such patient an effective amount of the cardiotonic N-[3-dimethylamino-2-(4-pyridinyl)-2-propenylidene]-N-methylmethaniminium salt (I) or pharmaceutically-acceptable acid-addition salt thereof. In a preferred embodiment of this aspect of the invention there is used as the cardiotonic N-[3-dimethylamino-2-(4-pyridinyl)-2-propenylidene]-N-methylmethaniminium chloride or pharmaceutically-acceptable acid-addition salt thereof, preferably the hydrochloride.

The N-[3-dimethylamino-2-(4-pyridinyl)-2-propenylidene]-N-methylmethaniminium salt (I) is useful both in the free base form (I) and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to form the hydrochloride. However, other appropriate pharmaceutically-acceptable salts within the scope of the invention are those derived from mineral acids such as hydrobromic acid, sulfuric acid, phosphoric acid and sulfamic acid; and organic acids such as acetic acid, lactic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, lactate, citrate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structures of the products produced by the process aspects of the invention were assigned on the basis of evidence provided by infrared, nuclear magnetic resonance and mass spectra, by chromatographic mobilities, and, by the correspondence of calculated and found values for the elemental analyses for representative examples.

The manner of making and using the instant invention will now be generally described so as to enable a person skilled in the art of chemistry to make and use the same, as follows:

In the process for preparing N-[3-dimethylamino-2-(4-pyridinyl)-2-propenylidene]-N-methylmethaniminium chloride hydrochloride from 4-picoline using at least three molar equivalents of phosgene per mole of 4-picoline and excess dimethylformamide, the reaction is preferably carried out by first adding the phosgene dropwise to the dimethylformamide at about −10° to 0° C. and then slowly adding, preferably dropwise, to this cold solution the 4-picoline, keeping the temperature below 25° C., preferably between 0° C. and 20° C., and then heating the reaction mixture at about 50°–80° C., preferably about 60°–65° C. Alternatively, the phosgene can be bubbled into the dimethylformamide kept at about 0° to 10° C. On cooling the reaction mixture to room temperature, said iminium chloride hydrochloride separates in practically quantitative yield. Preferably about ten volumes of dimethylformamide per volume of 4-picoline were used; however, we found the reaction to proceed satisfactorily with as little as five volumes of dimethylformamide per volume of 4-picoline. More dimethylformamide, viz., up to about twenty to twenty-five or more volumes of dimethylformamide per volume of 4-picoline can be used but to no particular advantage over the ten volume excess.

In the process of reacting N-[3-dimethylamino-2-(4-pyridinyl)-2-propenylidene]-N-methylmethaniminium chloride hydrochloride with Q—CH$_2$CONH$_2$ and at least three mole equivalents of base in anhydrous medium and then neutralizing the reaction mixture thereby converting the cationic metal salt of 5-Q-[3,4'-bipyridin]-6(1H)-one in solution to produce 5-Q-[3,4'-bipyridin]-6(1H)-one, which precipitates out of neutral and weakly acidic solution, the reaction is conveniently run by mixing the reactants so that the Q—CH$_2$CONH$_2$ is mixed with the base before the latter comes in contact with the imminium salt or else the latter will be partially hydrolyzed before it reacts with Q—CH$_2$CONH$_2$ and the yield of product will be lower. The reactants are heated at about 60°–100° C., conveniently on a steam bath until the reaction is complete. The reaction is carried out using a strong base in a lower-alkanol (one to four carbons) or a dipolar aprotic solvent, e.g., sodium methoxide, sodium hydride or anhydrous potassium carbonate in dimethylformamide; sodium methoxide, potassium hydroxide and 3:1 anhydrous potassium carbonate:potassium hydroxide in methanol; sodium hydride in dimethylformamide and tert-butanol; sodium methoxide in ethanol or isopropyl alcohol; sodium hydride in N,N-dimethylacetamide or pyridine; and the like. Other dipolar aprotic solvents useful would be acetonitrile and dimethyl sulfoxide. The product, 5-Q-[3,4'-bipyridin]-6(1H)-one as its cationic salt, sodium salt when sodium methoxide is used as base, is conveniently and preferably isolated from the cooled reaction mixture by filtration. The cationic salt form of the product is dissolved in water and in solution is neutralized by addition of acid, preferably acetic acid to a weakly acidic pH, viz. about 5.0 to 6.5, preferably about 6.0 to 6.5, to precipitate 5-Q-[3,4'-bipyridin]-6(1H)-one in very good over-all yields from 4-picoline.

The following examples will further illustrate the invention without, however, limiting it thereto.

EXAMPLE 1

N-[3-Dimethylamino-2-(4-pyridinyl)-2-propenylidene]-N-methylmethaniminium chloride hydrochloride Phosgene (213 ml., 98.7 g., 3.0 mole) was added dropwise with stirring and cooling to 1940 ml. (73 g., 25 moles) of dry, reagent grade dimethylformamide at −10° to 0° C. Cooling was discontinued and 4-picoline (97.3 ml., 93.1 g., 1.0 mole) was added slowly with stirring over a period of 5 minutes. An exothermic reaction ensued with the temperature rising to 35°–40° C. over the course of 1 hour. The mixture was heated with stirring at 60°–65° C. for 3 hours, then cooled to room temperature and filtered. The filtercake was washed successively with dimethylformamide and ether, then dried (50° C., 0.1 Torr., 4 hours). N-[3-dimethylamino-2-(4-pyridinyl)-2-propenylidene]-N-methylmethaniminium chloride hydrochloride was obtained as a pale-yellow crystalline solid, m.p. 150°–155° C. with decomposition (in a sealed capillary); the yield, was 271 g., 98%.

In another run using the same quantities of reactants and procedure but heating the reaction mixture at 60°–65° C. for 2 hours, there was obtained 269 g. (97% yield) of product. A 125 g. portion of the product was recrystallized from dry dimethylformamide, washed successively with two 100 ml. portions of dry dimethylformamide and two 100 ml. portions of ether, and dried on a rotary evaporator at 40° C. and 0.1 Torr. to produce 108 g. of N-[3-dimethylamino-2-(4-pyridinyl)-2-propenylidene]-N-methylmethaniminium chloride hydrochloride, m.p. 153°–158° C. with decomposition (in a sealed capillary).

EXAMPLE 2

5-Cyano-[3,4'-bipyridin]-6(1H)-one

A mixture containing 27.6 g. (0.1 mole) of [3-dimethylamino-2-(4-pyridinyl)-2-propenylidene]-N-methylmethaniminium chloride hydrochloride, 9.3 g. (0.11 mole) of α-cyanoacetamide, 41.5 g. (0.3 mole) of anhydrous potassium carbonate and 250 ml. of dry dimethylformamide was heated on a steam bath for one hour and the reaction mixture cooled. The precipitated solid, the potassium salt of the product, was collected, air-dried, dissolved in water and the resulting solution made weakly acid, pH of about 5, with acetic acid. The separated solid product was collected, washed successively with water, ethanol and ether, and then dried to yield 8 g. of 5-cyano-[3,4'-bipyridin]-6(1H)-one, m.p. >300° C. The above mother liquor was heated in vacuo to remove the liquids and the solid residue was dissolved in water (about 1 liter), the aqueous solution was neutralized with acetic acid to a pH of about 5; and, the separated solid was collected, washed successively with water, ethanol and ether, and dried in vacuo at 80° C. overnight to yield another 9 g. of 5-cyano-[3,4'-bipyridin]-6(1H)-one, m.p. >300° C.

EXAMPLE 3

5-Carbamyl-[3,4'-bipyridin]-6(1H)-one

A 12 g. portion of 50% sodium hydride (0.25 mole) dispersed in mineral oil is added to 11.2 g. (0.11 mole) of finely ground malonamide in 200 ml. of dried dimethylformamide and the mixture was stirred for 15 minutes at room temperature. To this stirred mixture was added 27.6 g. (0.1 mole) of 3-dimethylamino-2-(4-pyridinyl)-2-propen-1-ylidenedimethylammonium chloride hydrochloride whereupon an exothermic reaction causes the temperature to rise to about 65° C. The reaction mixture is heated on a steam bath for 1 hour and then cooled. The separated solid (sodium salt of product) was collected, dissolved in 1.7 liters of warm water and the aqueous solution was neutralized with acetic acid to a pH of about 5. The resulting precipitate was collected, washed successively with water, ethanol and ether, and dried in vacuo at 80° C. overnight to produce 16 g. of 5-carbamyl-[3,4'-bipyridin]-6(1H)-one, m.p., >300° C.

EXAMPLE 4

5-Cyano-[3,4'-bipyridin]-6(1H)-one

Phosgene (213 ml., 98.7 g., 3.0 mole) was added dropwise with stirring and cooling to 1940 ml. (25 moles) of dry, reagent grade dimethylformamide at −10° to 0° C. Cooling was discontinued and 4-picoline (93.1 g., 1.0 mole) was added with stirring over a period of 5 minutes. An exothermic reaction ensued with the temperature rising to 35°–40° C. over the course of 1 hour. The mixture was heated and stirred at 60°–65° C. for 3 hours, then cooled to room temperature. The precipitated salt was allowed to remain in the reaction vessel and the supernatant liquid was withdrawn by suction through a tube with a sintered-glass tip. The solid was washed with two 200 ml. portions of dimethylformamide and the wash liquid was also withdrawn by suction. The crystalline pale-yellow solid, viz., N-[3-dimethylamino-2-(4-pyridinyl)-2-propenylidene]-N-methylmethaniminium chloride hydrochloride, was treated with 2 liters of dry dimethylformamide. Malonamide (112 g., 1.1 mole) was added with stirring in one portion. Sodium methoxide (162 g., 3 moles) was added to the resultant slurry in one portion. An exothermic reaction occurred which caused the temperature to rise from 24° to 54° C. Concomitant with the exotherm was a phase change to a homogeneous solution. The charge was then heated at 95°–100° C. for 1 hour, cooled to 10°–20° C. and filtered; during the heating period the sodium salt of 5-cyano-[3,4'-bipyridin]-6(1H)-one began to separate. The resultant filtercake of said sodium salt was dissolved in 10 liters of warm tap water and the pH was adjusted to 5.5–6.5 with acetic acid. The precipitate is collected by filtration, washed with 2×500 ml. portions of water and dried (80° C., 1/3rd atmosphere, 16 hours) to produce, as a white to cream-colored solid, 160 g. (74% yield) of 5-cyano-[3,4'-bipyridin]-6(1H)-one, m.p. >300°.

EXAMPLE 5

N-[3-Dimethylamino-2-(4-pyridinyl)-2-propenylidene]-N-methylmethaniminium perchlorate hydroperchlorate A solution containing 15 g. of N-[3-dimethylamino-2-(4-pyridinyl)-2-propenylidene]-N-methylmethaniminium chloride hydrochloride dissolved in methanol (200 ml.) was treated with 5 ml. of 70% perchloric acid and the resulting mixture cooled. The separated solid was collected, dried, recrystallized from methanol, washed with ether and dried to produce 12 g. of N-[3-dimethylamino-2-(4-pyridinyl)-2-propenylidene]-N-methylmethaniminium perchlorate hydroperchlorate. This salt was made primarily for identification purposes. Its NMR spectrum correspond with that of its assigned structure.

Following the above procedure but using a corresponding molar equivalent quantity of a pharmaceutically-acceptable acid, e.g., methanesulfonic acid, in place of perchloric acid, it is contemplated that there can be obtained the corresponding pharmaceutically-acceptable acid-addition salt, e.g., N-[3,-dimethylamino-2-(4-pyridinyl)-2-propenylidene]-N-methylmethaniminium methanesulfonate monomethanesulfonate.

EXAMPLE 6

N-[3-dimethylamino-2-(4-pyridinyl)-2-propenylidene]-N-methylmethaniminium chloride To a solution kept at 0° to 5° C. and containing 20 g. of N-[3-dimethylamino-2-(4-pyridinyl)-2-propenylidene]-N-methylmethaniminium chloride hydrochloride dissolved in 100 ml. of methanol was added dropwise a solution containing 3.4 g. of sodium methoxide in 25 ml. of methanol. The separated sodium chloride was filtered off and the filtrate was stripped in vacuo at 30°–40° C. to remove the solvent. The solid residue was slurried in ethyl acetate and collected by filtration, washed with ether and dried. The solid was recrystallized from acetonitrile, washed with ether and dried at 80° C. in vacuo overnight to produce 5 g. of N-[3-dimethylamino-2-(4-pyridinyl)-2-propenylidene]-N-methylmethaniminum chloride, m.p. 233°–235° C. The NMR spectrum of this compound corresponded with that of its assigned structure.

The usefulness of N-[3-dimethylamino-2-(4-pyridinyl)-2-propenylidene]-N-methylmethaniminium salt (I) or pharmaceutically-acceptable acid-addition salt as cardiotonic agent is demonstrated by its effectiveness in standard cardiotonic test procedures, for example, in causing a significant increase in the contractile force of the isolated cat atria and papillary muscle. A detailed description of this test procedure appears in U.S. Pat. No. 4,072,746, issued Feb. 7, 1978.

When tested by the above-described isolated cat atria and papillary muscle procedure, N-[3-dimethylamino-2-(4-pyridinyl)-2-propenylidene]-N-methylmethaniminium chloride hydrochloride (I) at doses of 100 and 300 μg./ml. was found to cause significant increase, that is, 25° or greater, in papillary muscle force and a lesser increase, that is, between about 13–22%, in right atrial force, while causing a lower percentage increase (then that of papillary muscle force and right atrial force) in right atrial rate.

The present invention includes within its scope a cardiotonic composition for increasing cardiac contractility, said composition comprising a pharmaceutically-acceptable carrier and, as the active component thereof, the cardiotonic N-[3-dimethylamino-2-(4-pyridinyl)-2-propenylidene]-N-methylmethaniminium salt (I) or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with a least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavouring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. N-[3-Dimethylamino-2-(4-pyridinyl)-2-propenylidene]-N-methylmethaniminium salt in crystalline form having the formula

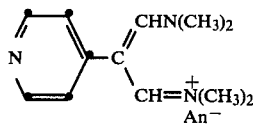

where An⁻ is an anion of a pharmaceutically-acceptable acid, or a pharmaceutically-acceptable acid-addition salt thereof.

2. N-[3-Dimethylamino-2-(4-pyridinyl)-2-propenylidene]-N-methylmethaniminium chloride in crystalline form.

3. N-[3-Dimethylamino-2-(4-pyridinyl)-2-propenylidene]-N-methylmethaniminium chloride hydrochloride in crystalline form.

4. A cardiotonic composition for increasing cardiac contractility, said composition comprising a pharmaceutically-acceptable inert carrier and, as the active component thereof, an effective amount for increasing cardiac contractility of the cardiotonic N-[3-dimethylamino-2-(4-pyridinyl)-2-propenylidene]-N-methylmethaniminium salt or pharmaceutically-acceptable acid-addition salt thereof.

5. A composition according to claim 4 where the active component is N-[3-dimethylamino-2-(4-pyridinyl)-2-propenylidene]-N-methylmethaniminium chloride hydrochloride.

6. The method for increasing cardiac contractility in a patient requiring such treatment which comprises administering orally or parenterally in a solid or liquid dosage form to such patient an effective amount for increasing cardiac contractility of the cardiotonic N-[3-dimethylamino-2-(4-pyridinyl)-2-propenylidene]-N-methylmethaniminium salt or pharmaceutically-acceptable acid-addition salt thereof.

7. The method according to claim 6 wherein the cardiotonic is N-[3-dimethylamino-2-(4-pyridinyl)-2-propenylidene]-N-methylmethaniminium chloride hydrochloride.

8. The process which comprises slowly mixing 4-picoline with at least three mole equivalents of phosgene per mole of 4-picoline and at least a five to ten volume excess of dimethylformamide per volume of 4-picoline keeping the temperature below 25° C., heating the mixture at about 50°–80° C., cooling the reaction mixture and collecting the separated N-[3-dimethylamino-2-(4-pyridinyl)-2-propenylidene]-N-methylmethaniminium chloride hydrochloride in crystalline form.

9. The process which comprises mixing N-[3-dimethylamino-2-(4-pyridinyl)-2-propenylidene]-N-methylmethaniminium chloride hydrochloride with a mixture of Q-CH$_2$CONH$_2$ and at least three mole equivalents of base in an anhydrous medium, heating the reaction mixture at about 60°–100° C. and then neutralizing the reaction mixture to produce 5-Q-[3,4'-bipyridin]-6(1H)-one, where Q is cyano or carbamyl.

10. The process according to claim 9 where α-cyanoacetamide is used to produce 5-cyano-[3,4'-bipyridin]-6(1H)-one.

11. The process according to claim 9 where malonamide is used to produce 5-carbamoyl-[3,4'-bipyridin]-6(1H)-one.

12. The process which comprises the steps of first slowly mixing 4-picoline with at least three mole equivalents of phosgene per mole of 4-picoline and at least a five to ten volume excess of dimethylformamide per volume of 4-picoline keeping the temperature below 25° C., heating the mixture at about 50°–80° C., cooling the reaction mixture and collecting the separated N-[3-dimethylamino-2-(4-pyridinyl)-2-propenylidene]-N-methylmethaniminium chloride hydrochloride in crystalline form and then mixing said chloride hydrochloride with a mixture of Q-CH$_2$CONH$_2$ and at least three mole equivalents of base is an anhydrous medium, heating the reaction mixture at about 60°–100° C. and then neutralizing the reaction mixture to produce 5-Q-[3,4'-bipyridin]-6(1H)-one, where Q is cyano or carbamyl.

13. The process according to claim 12 where α-cyanoacetamide is used in the second step to produce 5-cyano-[3,4'-bipyridin]-6(1H)-one.

14. The process according to claim 12 wherein malonamide is used in the second step to produce 5-carbamyl-[3,4'-bipyridin]-6(1H)-one.

* * * * *

UNITED STATES PATENT AND TRADEMARK OFFICE
CERTIFICATE OF CORRECTION

PATENT NO. : 4,264,609
DATED : April 28, 1981
INVENTOR(S) : K.O. Gelotte and C.J. Opalka, Jr.

It is certified that error appears in the above–identified patent and that said Letters Patent are hereby corrected as shown below:

Column 10, Claim 11, line 37, "carbamoyl" should read -- carbamyl --.

Column 10, Claim 12, line 50, "is" should read -- in --.

*Signed and Sealed this*

*Thirty-first* Day of *August 1982*

[SEAL]

Attest:

GERALD J. MOSSINGHOFF

Attesting Officer    Commissioner of Patents and Trademarks